United States Patent [19]

Mallams et al.

[11] 3,978,214

[45] Aug. 31, 1976

[54] NOVEL 4,6-DI-O-(AMINOGLYCOSYL)-2-DEOXYSTREPTAMINE, METHOD FOR ITS MANUFACTURE, METHOD FOR ITS USE AS AN ANTIPROTOZOAL AGENT AND COMPOSITIONS USEFUL THEREOF

[75] Inventors: Alan K. Mallams, West Orange, N.J.; David Huw Davies, Macclesfield, England

[73] Assignee: Schering Corporation, Kenilworth, N.J.

[22] Filed: May 2, 1975

[21] Appl. No.: 574,074

[52] U.S. Cl.................................. 424/180; 536/4; 536/17
[51] Int. Cl.[2] ................. A61K 31/71; C07H 15/22
[58] Field of Search ...... 260/210 AB, 210 S, 210 R; 424/180

[56] References Cited

UNITED STATES PATENTS

| | | | |
|---|---|---|---|
| 3,832,286 | 8/1974 | Weinstein et al............. | 260/210 AB |
| 3,880,828 | 4/1975 | Mallams....................... | 260/210 AB |

*Primary Examiner*—Johnnie R. Brown
*Attorney, Agent, or Firm*—Mary S. King

[57] ABSTRACT

The novel aminoglycoside, 0-2-amino-2,3,4-trideoxy-α-D-glycero-hex-4-enopyranosyl-(1 → 4)-garamine, is prepared by treating Aminoglycoside 66-40C with aqueous acid followed by treatment with a hydride donor reducing agent. Pharmaceutical compositions of the novel aminoglycoside and its pharmaceutically acceptable acid addition salts are described as well as their use as antiprotozoal agents.

4 Claims, No Drawings

NOVEL 4,6-DI-O-(AMINOGLYCOSYL)-2-DEOXYSTREP-TAMINE, METHOD FOR ITS MANUFACTURE, METHOD FOR ITS USE AS AN ANTIPROTOZOAL AGENT AND COMPOSITIONS USEFUL THEREOF

FIELD OF INVENTION

This invention relates to a novel composition-of-matter, to a method for its manufacture, to pharmaceutical formulations thereof, and to the method for its use as an antiprotozoal agent.

More specifically, this invention relates to a novel 4,6-di-O-(aminoglycosyl)-2-deoxystreptamine having anti-protozoal activity, to a method for its manufacture, to pharmaceutical compositions comprising said 4,6-di-O-(amino-glycosyl)-2-deoxystreptamine or an acid addition salt thereof and to methods for their use in treating protozoal infections.

In particular, this invention relates to the novel aminoglycoside O-2-amino-2,3,4-trideoxy-α-D-glycero-hex-4-enopyranosyl-(1 → 4)-garamine having antiproozoal activity. This invention also relates to the process for the preparation of O-2-amino-2,3,4-trideoxy-α-D-glycero-hex-4-enopyranosyl-(1 → 4)-garamine and its acid addition salts, to pharmaceutical compositions thereof and to the method of using said pharmaceutical compositions to elicit an antiprotozoal response in a warm-blooded animal having a susceptible protoazoal infection.

GENERAL DESCRIPTION OF INVENTION

Composition of Matter Aspect

In its composition-of-matter aspect, this invention relates to a novel aminoglycoside of a class generically known in the art as 4,6-di-O-(aminoglycosyl)-2-deoxystreptamines.

In particular this invention relates to a compound selected from the group consisting of O-2-amino-2,3,4-trideoxy-α-D-glycero-hex-4-enopyranosyl-(1 → 4)-garamine, said compound being represented by the following formula I:

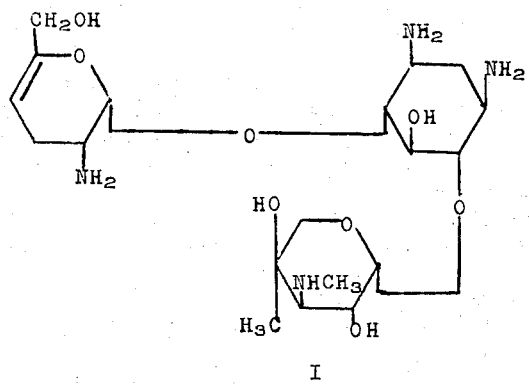

I and the pharmaceutically acceptable acid addition salts thereof.

The O-2-amino-2,3,4-trideoxy-α-D-glycero-hex-4-enopyranosyl-(1 → 4)-garamine of this invention is characterized as a colorless, amorphous solid, which is soluble in water, alcohols, and is particularly soluble in dimethylformamide.

Also included in the composition-of-matter aspect of this invention are the pharmaceutically acceptable acid addition salts of O-2-amino-2,3,4-trideoxy-α-D-glycero-hex-4-enopyranosyl-(1 → 4)-garamine. These salts are prepared according to known procedures, such as by neutralizing the free base with the appropriate acid, usually to about pH 5. Suitable acids for this purpose include acids such as hydrochloric, sulphuric, phosphoric, hydrobromic and the like.

The acid addition salts of O-2-amino-2,3,4-trideoxy-α-D-glycero-hex-4-enopyranosyl-(1 → 4)-garamine are characterized by being white solids which are soluble in water and insoluble in most polar and non-polar organic solvents.

The novel compound of this invention, i.e. O-2-amino-2,3,4-trideoxy-α-D-glycero-hex-4-enopyranosyl-(1 → 4)-garamine, and its pharmaceutically acceptable acid addition salts, exhibit a spectrum of anti-bacterial activity in vitro against gram-positive bacteria e.g. *Staphylococcus aureus* (strains 209P, Wood, Ziegler and 59N); *Bacillus subtilis* (strain 6633). Our compound also exhibits antibacterial activity in vitro against gram-negative bacteria e.g. *Pseudomonas aeruginosa* (strains NRRL 3223; and Stone 39), *Escherichia coli* (strains ATCC 10536 and 1574-1). Thus the compounds of our invention may be used to "sterilize" equipment such as in operating rooms and in hospital wards.

In addition to exhibiting antibacterial activity, our compound advantageously also exhibits antiprotozoal activity. When tested in vitro against *Trichomonas vaginalis*, O-2-amino-2,3,4'-trideoxy-α-D-glycero-hex-4-enopyranosyl-(1 → 4)-garamine exhibits cidal activity at less than 10 mcg./ml. When tested in vitro against *Entamoeba histolytica* (J.H. strain). it exhibits a minimal inhibitory concentration (MIC) of 10 mcg./ml. and a minimal cidal concentration (MCC) of 20 mcg./ml.

Process Aspect of the Invention

The process aspect of this invention relates to the process for the preparation of O-2-amino-2,3,4-trideoxy-α-D-glycero-hex-4-enopyranosyl-(1 → 4)-garamine which comprises the reaction of Aminoglycoside 66-40C in aqueous acid followed by the reaction of the thereby formed intermediate in situ with a hydride donor reducing agent selected from the group consisting of sodium cyanoborohydride, lithium cyanoborohydride, morpholinoborane, dialkylaminoborane and tetraalkylammonium cyanoborohydride.

The requisite starting material of this process, i.e. aminoglycoside 66-40C, is a compound represented by the following formula II:

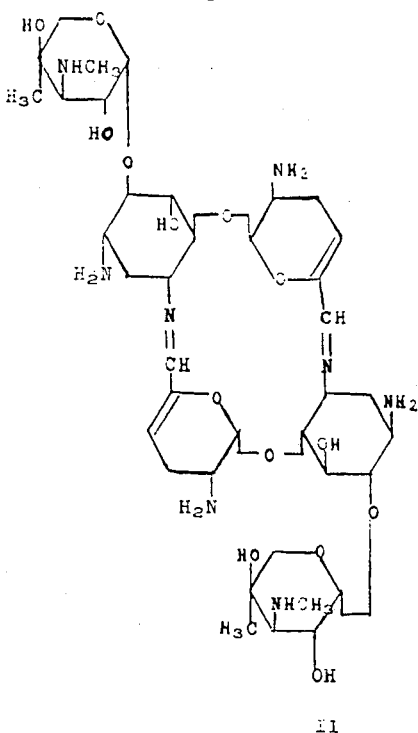

II

Aminoglycoside 66-40C is a minor component of the crude antibiotic complex produced by the fermentation of *Micromonospora inyoensis* (ref. British Pat. No. 1,274,518) and is isolated via chromatographic techniques as described hereinafter in Preparations I and II. Aminoglycoside 66-40C as shown in Formula II, has a dimeric structure containing α,β-unsaturated imine groups. When, according to the process of this invention, Aminoglycoside 66-40C is reacted with aqueous acid, such as aqueous phosphoric acid, it hydrolyses into a monomer producing an aldehyde intermediate in situ which, upon treatment with a metal hydride according to our process, is reduced to the corresponding hydroxyl derivative of this invention, i.e. O-2-amino-2,3,4-trideoxy-α-D-glycero-hex-4-enopyranosyl-(1 → 4)-garamine, which is isolated and purified via chromatographic techniques such as described in detail in Example I hereinbelow.

Acids which are useful in our process include the general class of mineral acids such as hydrochloric, sulphuric, phosphoric and the like, preferably phosphoric acid.

Usually our process is carried out at room temperature although it may be carried out at temperatures in the range of from 25°C to about 100°C. Our process may be monitored for completion by the utilization of $^{13}$C magnetic resonance (CMR).

The invention described hereinabove is illustrated in detail hereinbelow in the Preparations and Examples which should not be construed as limiting the scope of our invention.

PREPARATION I

Crude Mixture of the Minor Components of the Fermentation of *Micromonospora inyoensis*

The crude antiobiotic complex produced by the fermentation of *Micromonospora inyoensis* (ref. British Pat. No. 1,274,518) is subjected to chromatographic separation on silica gel. The complex is dissolved in the lower phase of a solvent mixture consisting of chloroform, methanol and concentrated ammonium hydroxide (1:1:1). Add this solution to the silica gel column and elute the column with the same solvent mixture. Collect the fractions of eluant and monitor the fractions by thin-layer chromatography on silica gel plates using the same solvent system as that used on the column. Combine the fractions containing material having the same mobility on thin layer and evaporate the fractions to dryness to obtain two fractions of active material. The first (least polar) fraction eluted contains substantially pure sisomicin and the last (most polar) fraction contains the crude mixture of the minor components of the fermentation.

PREPARATION II

Separation of Aminoglycoside 66-40C from Co-produced Antibiotics

To a chromatographic column of about 160 cm. in length by about 5 cm. in diameter containing silica gel, add 9.65 g of the crude mixture of the minor components of the fermentation of *Micromonospora inyoensis* dissolved in a solution of chloroform — methanol — 7% ammonium hydroxide (1:2:1). Elute the column with the same solvent system. Combine the eluant containing Aminoglycoside 66-40C as determined by thin layer chromatography and evaporate to a residue. Take the resultant residue up in water and pass down a column of Amberlite IRA 401S (OH$^-$) resin and lyophilize to obtain 1.8 g of Aminoglycoside 66-40C as a colorless amorphous solid. m.p.: 185°–205°C; m/e 856 (M $.^+$) MW 847 (osmometry) (calc'd. MW 856); $[\alpha]_D^{26}$ + 112.5° (c0.3%, H$_2$O); I.R.: $\nu$ max (KCl) 3300, 1670, 1640, 1620, 1025 cm.$^{-1}$; U.V.: λ max (CH$_3$OH) 248 mμ (ε22,000); C.D.: $[\theta]_{280}$ − 7,720 (CH$_3$OH); $[\theta]_{290}$ − 23,400 (TACu); $[\theta]_{290}$ − 18,620 (Cupra A); N.M.R.: δ (D$_2$O) 1.22 (6H, s, 4″—CH$_3$), 2.52 (6H, s, 3′λ′—NCH$_3$), 5.15 (2H, d, J4Hz, H$_1$″), 5.48 (2H, m, H$_4$′), 5.50 (2H, d, J2Hz, H$_1$′) and 7.56 ppm. (2H, s, H$_6$′).

EXAMPLES

EXAMPLE I

O-2-Amino-2,3,4-trideoxy-α-D-glycero-hex-4-enopyranosyl-(1 → 4)-garamine

Dissolve 200 mg. of Aminoglycoside 66-40C in 20 ml. of distilled water and acidify the solution to about a pH of 3–4 by the addition of phosphoric acid. Stir the reaction mixture at 25°C for 30 minutes and then add 200 mg. sodium cyanoborohydride and stir another 30 minutes. Pass the solution down Amberlite IRA 401S (OH$^-$) resin. Acidify the eluate with acetic acid and evaporate to dryness. Chromatograph the residue on a silica gel column (70 × 1cm.) using the lower phase of a chloroform — methanol — concentrated ammonium hydroxide solution (1:1:1) as the eluant. Evaporate the eluted material and take the resultant residue up in water and pass down Amberlite IRA 401S (OH$^-$) resin and lyophilize to obtain 70 mg. of O-2-amino-2,3,4-trideoxy-α-D-glycero-hex-4-enopyranosyl-(1 → 4)-garamine, a colorless amorphous solid; $[\alpha]_D^{26}$ + 163.9° (c 0.3% H$_2$O); C.D.: $[\theta]_{290}$−8,400 (TACu);m/e 448(M.$^+$), I.R.$\nu$ max (KCl) 3300, 2900, 1680, 1060 cm.$^{-1}$, N.M.R. δ (D$_2$O) 1.24 (3H,s,4″-CH$_3$), 2.56 (3H,s,3″-NCH$_3$), 3.99 (2H,s, 6′-CH$_2$), 5.06 (1H, m, H$_4$′), 5.13 (1H,d, J4Hz,H$_1$″) and 5.41 ppm. (1H,d, J2Hz,H$_1$′)

EXAMPLE II

Acid Addition Salts

A. Sulfate salts (Sulfuric Acid Addition Salts)

Dissolve 5.0 gms of O-2-amino-2,3,4-trideoxy-α-D-glycero-hex-4-enopyranosyl-(1 → 4)-garamine in 25 ml of water and adjust the pH of the solution of 5.0 with 1N sulfuric acid. Pour into about 300 ml of methanol with vigorous agitation, continue the agitation for about 10-20 minutes and filter. Wash the precipitate with methanol and dry at about 60°C in vacuo to obtain O-2-amino-2,3,4-trideoxy-α-D-glycero-hex-4-enopyranosyl-(1 → 4)-garamine sulfate.

B. Hydrochloride salts

Dissolve 5.0 g of O-2-amino-2,3,4-trideoxy-α-D-glycero-hex-4-enopyranosyl-(1 → 4)-garamine in 2.5 ml. of water. Acidify with 2N hydrochloric acid to pH 5. Lyophilize to obtain O-2-amino-2,3,4-trideoxy-α-D-glycero-hex-4-enopyranosyl-(1 → 4)-garamine hydrochloride.

The present invention includes within its scope pharmaceutical compositions comprising O-2-amino-2,3,4-trideoxy-α-D-glycero-hex-4-enopyranosyl-(1 → 4)-garamine and the pharmaceutically acceptable acid addition salts thereof in association with a compatible, pharmaceutically acceptable carrier or coating. Also included within our invention is the method of eliciting an antiprotozoal response in a warm-blooded animal having a susceptible protozoal infection which comprises administering to said animal a non-toxic, antiprotozoally effective amount of O-2-amino-2,3,4-trideoxy-α-D-glycero-hex-4-enopyranosyl-(1 → 4)-garamine or of a pharmaceutically acceptable acid addition salt thereof.

The antiprotozoal compositions of this invention may be administered orally in the form of elixirs, tablets, capsules, or topically in the form of creams, ointments suppositories and the like. The active ingredient is normally combined with conventional pharmaceutical diluents and carriers which are based upon the desired route of administration. Further, O-2-amino-2,3,4-trideoxy-α-D-glycero-hex-4-enopyranosyl-(1 → 4)-garamine, can if desired, be combined with other therapeutically active compositions such as for example anti-anxiety agents, it being known that infections and infestations often cause anxiety reactions in animal species.

The individual unit dosage and frequency of administration is determined by the route of administration and by the nature and severity of the protozoal infection for which relief is sought, as well as upon the age, weight, species and underlying physical condition of the animal species being treated. The dosage to be administered should be non-toxic, yet pharmaceutically effective in alleviating the symptoms of protozoal infections. Generally, for the topical treatment of protozoal infections, the compositions are designed to contain from about 0.5 to 5% of O-2-amino-2,3,4-trideoxy-α-D-glycero-hex-4-enopyranosyl-(1 → 4)-garamine or a non-toxic pharmaceutically acceptable salt thereof. Generally, for the treatment of oral protozoal infections, the compositions are administered so as to give a daily dose of from 10 to about 40 mg/kg of O-2-amino-2,3,4-trideoxy-α-D-glycero-hex-4-enopyranosyl-(1 → 4)-garamine or a non-toxic pharmaceutically acceptable salt thereof.

The following Examples illustrate the pharmaceutical compositions according to the invention.

EXAMPLE 3

| Topical Cream | gms/kg. |
| --- | --- |
| O-2-amino-2,3,4-trideoxy-α-D-glycero-hex-4-enopyranosyl-(1 → 4)-garamine (as the sulfate) | 5–50* |
| Stearic Acid | 60 |
| Propylene Glycol Monostearate | 100 |
| Isopropyl Myristate | 80 |
| Polysorbate 40 | 60 |
| Sorbitol Solution | 20 |
| Propylene glycol | 30.0 |
| Methylparaben | 1.0 |
| Butylparaben | 4.0 |
| Water Purified to make | 1.0 kg |

*Based on theoretical 100% purity

PROCEDURE

Cream

Step
1. To a suitable mixing vessel add the stearic acid, propylene glycol monostearate, isopropyl myristate and polysorbate 40 and heat to 85°–90°C. To this add the butylparaben.
2. To a second mixing vessel charge the water and heat to 90°. Charge to this the sorbitol solution and propylene glycol and methyl paraben.
3. Pump the wax phase (step 1) into the water phase (step 2) and agitate and emulsify and cool to 50°.
4. Dissolve the O-2-amino-2,3,4-trideoxy-α-D-glycero-hex-4-enopyranosyl-(1 → 4)-garamine in 2 liters of 50°C purified water and add to the emulsion. Mix until uniform.

EXAMPLE 4

| Oral Syrup | gms/liter |
| --- | --- |
| O-2-amino-2,3,4-trideoxy-α-D-glycero-hex-4-enopyranosyl-(1 → 4)-garamine (as the sulfate) | 100–400* |
| Sugar standard granulated | 550.00 |
| Glycerin USP | 150.00 |
| Methylparaben | 0.50 |
| Propylparaben | 0.10 |
| Propylene glycol | 50.00 |
| Flavor | 0.50–1.00~ |
| Alcohol USP | 65.00 |
| Dyes | 0.03–0.02~ |
| Water Purified USP to make | 1.00 l. |

*Based on theoretical 100% purity

PROCEDURE

Syrup

Step
1. Dissolve the O-2-amino-2,3,4-trideoxy-α-D-glycero-hex-4-enopyranosyl-(1 → 4)-garamine (as the sulfate), granulated sugar and sorbital solution in approximately 350 ml of purified water contained in a suitable mixing vessel and mix until a solution is obtained.
2. Dissolve the parabens in a mixture of the glycerin, propylene glycol and alcohol. To this add the suitable flavor and dye.
3. Pump the paraben phase (step 2) into the active phase (step 1) — mix and then bring to volume with purified water.

We claim:

1. A compound selected from the group consisting of O-2-amino-2,3,4-trideoxy-α-D-glycero-hex-4-enopyranosyl-(1 → 4)-garamine as defined by the following structural formula:

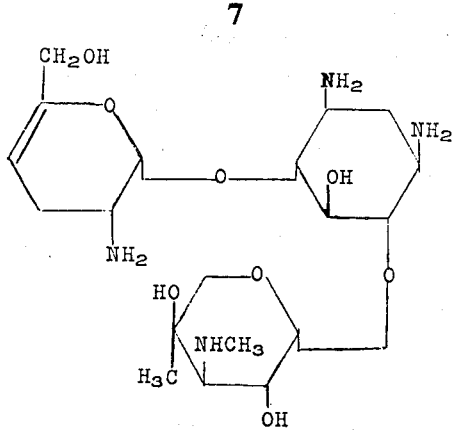

and the pharmaceutically acceptable acid addition salts thereof.

2. The process for the preparation of O-2-amino-2,3,4-trideoxy-α-D-glycero-hex-4-enopyranosyl-(1 → 4)-garamine which comprises; the reaction of Aminoglycoside 66-40C in aqueous mineral acid followed by the reaction of the thereby formed intermediate in situ with a hydride donor reducing agent selected from the group consisting of sodium cyanoborohydride, lithium cyanoborohydride, morpholinoborane, dialkylaminoborane, and tetraalkylammonium cyanoborohydride.

3. The method of eliciting an anti-protozoal response in a warm-blooded animal having a susceptible protozoal infection which comprises administering to said animal a non-toxic antiprotozoally effective amount of a compound selected from the group consisting of O-2-amino-2,3,4-trideoxy-α-D-glycero-hex-4-enopyranosyl-(1 → 4)-garamine and the pharmaceutically acceptable acid addition salts thereof.

4. A pharmaceutical composition comprising an antiprotozoally effective amount of a compound selected from the group consisting of O-2-amino-2,3,4-trideoxy-α-D-glycero-hex-4-enopyranosyl-(1 → 4)-garamine and the pharmaceutically acceptable acid addition salts thereof; together with a non-toxic pharmaceutically acceptable carrier.

* * * * *

UNITED STATES PATENT AND TRADEMARK OFFICE
CERTIFICATE OF CORRECTION

PATENT NO. : 3,978,214
DATED : August 31, 1976
INVENTOR(S) : Alan K. Mallams and David Huw Davies It is certified that error appears in the above—identified patent and that said Letters Patent are hereby corrected as shown below:

Column 1, line 23, "antiproozoal activity." should read ---antiprotozoal activity.---; line 30, "protoazoal" should read, ---protozoal---. Column 4, lines 36 and 37, "2.52 (6H, s, 3'λ —" should read ---2.52 (6H, s, 3"— ---.

Signed and Sealed this

Fourteenth Day of December 1976

[SEAL]

Attest:

RUTH C. MASON
Attesting Officer

C. MARSHALL DANN
Commissioner of Patents and Trademarks